US011013503B2

(12) United States Patent
Pedicini

(10) Patent No.: US 11,013,503 B2
(45) Date of Patent: May 25, 2021

(54) ORTHOPEDIC DEVICE DELIVERING A CONTROLLED, REPEATABLE IMPACT

(71) Applicant: DePuy Synthes Products, Inc., Raynham, MA (US)

(72) Inventor: Christopher Pedicini, Franklin, TN (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/789,493

(22) Filed: Oct. 20, 2017

(65) Prior Publication Data

US 2018/0338751 A1     Nov. 29, 2018

Related U.S. Application Data

(60) Provisional application No. 62/511,811, filed on May 26, 2017.

(51) Int. Cl.
| | |
|---|---|
| *A61B 17/92* | (2006.01) |
| *A61F 2/46* | (2006.01) |
| *A61B 17/02* | (2006.01) |
| *A61B 5/00* | (2006.01) |
| *A61B 17/16* | (2006.01) |
| *A61B 5/103* | (2006.01) |

(52) U.S. Cl.
CPC ............ *A61B 17/025* (2013.01); *A61B 17/92* (2013.01); *A61F 2/4603* (2013.01); *A61F 2/4607* (2013.01); *A61B 5/1036* (2013.01); *A61B 5/4528* (2013.01); *A61B 17/1604* (2013.01); *A61B 2017/922* (2013.01); *A61B 2560/0209* (2013.01); *A61F 2002/469* (2013.01); *A61F 2002/4681* (2013.01)

(58) Field of Classification Search
USPC .......................................... 173/203
See application file for complete search history.

(56) References Cited

U.S. PATENT DOCUMENTS

| | | | |
|---|---|---|---|
| 5,057,112 A | 10/1991 | Sherman et al. | |
| 5,152,352 A | 10/1992 | Mandanis | |
| 6,938,705 B2 | 9/2005 | Kikuchi | |
| 7,001,393 B2 | 2/2006 | Schwenke et al. | |
| 8,393,409 B2 | 3/2013 | Pedicini | |

(Continued)

OTHER PUBLICATIONS

International Search Report and Written Opinion for PCT/US18/17763 dated May 7, 2018 (11 pages).

*Primary Examiner* — Samuel S Hanna

(57) ABSTRACT

In an illustrative embodiment, a motor-driven orthopedic impacting tool for orthopedic impacting in the hips, knees, shoulders and the like may be capable of holding a surgical implement such as a broach, chisel, or other end effector, which when gently tapped in a cavity with controlled percussive impacts, can expand the size or volume of an opening of the cavity or facilitate removal of the surgical implement from the opening. A stored-energy drive mechanism may store potential energy and then release it to launch a launched mass or striker to communicate a striking force to an adapter in either a forward or reverse direction. The tool may further include a combination anvil and adapter and an energy adjustment mechanism to adjust the striking force the launched mass delivers to the adapter.

24 Claims, 13 Drawing Sheets

(56) References Cited

U.S. PATENT DOCUMENTS

| | | |
|---|---|---|
| 8,602,124 B2 | 12/2013 | Pedicini |
| 8,695,726 B2 | 4/2014 | Pedicini |
| 8,936,105 B2 | 1/2015 | Pedicini |
| 8,936,106 B2 | 1/2015 | Pedicini |
| 9,034,004 B2 | 5/2015 | Pansky |
| 9,901,354 B2 | 2/2018 | Pedicini |
| 2004/0026097 A1* | 2/2004 | Hecht .................. B25D 11/005 173/114 |
| 2009/0236387 A1* | 9/2009 | Simonelli ............. B25C 5/1668 227/8 |
| 2011/0245736 A1 | 10/2011 | Foehrenbach |
| 2012/0265111 A1 | 10/2012 | Glenzer et al. |
| 2013/0161050 A1* | 6/2013 | Pedicini ................ B25D 17/00 173/201 |
| 2015/0196343 A1 | 7/2015 | Donald et al. |
| 2016/0096259 A1* | 4/2016 | Pedicini .................. B25C 1/047 227/146 |
| 2016/0199199 A1 | 7/2016 | Pedicini |
| 2017/0100829 A1* | 4/2017 | Pedicini ................ B25C 1/047 |
| 2018/0055518 A1 | 3/2018 | Pedicini |

\* cited by examiner

ORTHOPEDIC DEVICE DELIVERING A CONTROLLED, REPEATABLE IMPACT

RELATED APPLICATIONS

This application claims priority to U.S. Provisional Patent Application Ser. No. 62/511,811 entitled "Orthopedic impacting Device," filed May 26, 2017. This application is related to the following prior patent applications directed to Orthopedic Impacting Devices: U.S. patent application Ser. No. 13/790,870 entitled "Electric Motor Driven Tool for Orthopedic Impacting," filed Mar. 8, 2013, now U.S. Pat. No. 8,602,124; U.S. patent application Ser. No. 12/980,329 entitled "Electric Motor Driven Tool for Orthopedic Impacting," filed Dec. 29, 2010, now U.S. Pat. No. 8,695,726; U.S. patent application Ser. No. 14/332,790 entitled "Electric Motor Driven Tool for Orthopedic Impacting," filed Jul. 16, 2014, now U.S. Pat. No. 8,936,106; U.S. patent application Ser. No. 13/466,870 entitled "Electric Motor Driven Tool for Orthopedic impacting," filed May 8, 2012, now U.S. Pat. No. 8,393,409; U.S. patent application Ser. No. 14/332,767 entitled "Electric Motor Driven Tool for Orthopedic Impacting," filed Jul. 16, 2014, now U.S. Pat. No. 8,936,105; U.S. patent application Ser. No. 14/250,102 entitled "Electric Motor Driven Tool for Orthopedic Impacting," filed Apr. 10, 2014; and U.S. patent application Ser. No. 14/992,781 entitled "Electric Motor Driven Tool for Orthopedic Impacting," filed Jan. 11, 2016. All above identified applications are hereby incorporated by reference in their entireties.

BACKGROUND

The present disclosure relates to locally powered tools for impacting in surgical applications such as orthopedic procedures, and, more particularly, to a hand-held motor driven tool for bidirectional, surgical impacting that is driven by a launched mass to provide controlled, repeatable impacts to a broach or other end effector.

In the field of orthopedics, prosthetic devices, such as artificial joints, are often implanted or seated in a patient's bone cavity. The cavity is typically formed during surgery before a prosthesis is seated or implanted, for example, a physician may remove and or compact existing bone to form the cavity. The prosthesis usually includes a stem or other protrusion that is inserted into the cavity.

To create the cavity, a physician may use a broach conforming to the shape of the stem of the prosthesis. Solutions known in the art include providing a handle with the broach for manual hammering by the physician during surgery to impel the broach into the implant area. Unfortunately, this approach is crude and notoriously imprecise, leading to unnecessary mechanical stress on the bone. The results can be unpredictable and depend on the skill of a particular physician. Historically, this approach will in many cases result in inaccuracies in the location and configuration of the cavity. Additionally, the surgeon is required to expend an unusual amount of physical force and energy to hammer the broach and to manipulate the bones and prosthesis. Most importantly, this approach carries with it the risk that the physician will cause unnecessary further trauma to the surgical area and damage otherwise healthy tissue, bone structure and the like.

Another technique for creating the prosthetic cavity is to drive the broach pneumatically, that is, by compressed air. This approach is disadvantageous in that it prevents portability of an impacting tool, for instance, because of the presence of a tethering air-line, air being exhausted from a tool into the sterile operating field and fatigue of the physician operating the tool. This approach, as exemplified in U.S. Pat. No. 5,057,112, does not allow for precise control of the impact force or frequency and instead functions very much like a jackhammer when actuated. Again, this lack of any measure of precise control makes accurate broaching of the cavity more difficult and can lead to unnecessary patient complications and trauma.

A third technique relies on computer-controlled robotic arms for creating the cavity. While this approach overcomes the fatiguing and accuracy issues, it suffers from having a very high capital cost and additionally removes the tactile feedback that a surgeon can get from a manual approach.

A fourth technique relies on the inventor's own, previous work which uses a linear compressor to compress air on a single stroke basis and then, after a sufficient pressure is created, to release the air through a valve and onto a striker. This then forces the striker to travel down a guide tube and impact an anvil, which holds the broach and or other surgical tool. However, this arrangement, due to the pressure of the air, results in the generation of large forces on the gear train and linear motion converter components, which large forces lead to premature wear on components.

A fifth technique also relies on the inventor's own, previous work which uses a linear actuator to create a vacuum against a detent. After a sufficient vacuum volume is generated, the detent releases a striker and allows the striker to travel down a guide tube and impact an anvil, which holds a broach or other surgical tool. This arrangement, however, puts undue stress on the drive components and is subject to environmental conditions, such as the atmospheric pressure. Furthermore, this technique is limited in its ability to generate a reverse or rearward impact.

Consequently, there exists a need for an impacting tool having an improved drive assembly that overcomes the various disadvantages of existing systems and previous solutions of the inventor.

SUMMARY OF ILLUSTRATIVE EMBODIMENTS

In view of the foregoing disadvantages, an electric motor-driven orthopedic impacting tool is provided for orthopedic impacting in hips, knees, shoulders and the like. The tool is capable of holding a broach, chisel, or other end effector and gently tapping the broach, chisel or other end effector into the cavity with controlled percussive impacts, resulting in a better fit for the prosthesis or the implant. Further, the control afforded by such an electrically manipulated broach, chisel, or other end effector allows adjustment of the impact settings according to a particular bone type or other profile of a patient. The tool additionally enables proper seating and in the case of bidirectional movement the removal of the prosthesis or the implant into or out of an implant cavity and advantageously augments the existing surgeon's skill in guiding the instrument.

In certain embodiments, an electric motor-driven orthopedic impacting tool includes a local power source (such as a battery or fuel cell), a motor assembly, a controller, a housing, a stored-energy drive system or mechanism such as a gas or mechanical spring capable of storing and releasing potential energy, and a striker energized by the stored-energy drive system to be operational in a forward and/or a rearward direction, where the striker is capable of generating an impact force to a surgical implement. The motor assembly may include a linear drive. In another example, the motor assembly may include a rotary drive and a method of converting rotary motion to linear motion (hereafter referred to as a linear motion converter). The tool may further deliver focused illumination to the surgery area by way of a semiconductor light source, such as an LED, or traditional incandescent light source. A handle may be provided for handling the tool by a physician, or a suitable mount interface for integrating the tool into a robotic assembly. A local power source such as a battery is also included. As is typical, at least some of the various components are preferably contained within a housing. The tool is capable of applying cyclic, repeatable impact forces on a broach, chisel, or other end effector, or an implant. Given the repeatability of the impact force, finely tuning the impact force to a number of levels is also contemplated. To this end a number of springs may be provided together with the device in a kit format, whereby different visually-coded springs may be removably introduced to the tool as needed during a surgical procedure to provide for a range of drive forces.

Regarding the stored-energy drive system, in some embodiments the system is actuatable by a motor in combination with a cam and a worm radially protruding from the cam, which rotates in a first direction compressing a spring, thus storing potential energy within the stored-energy drive system. The cam, for example, may be a barrel cam or cylindrical cam. The cam further continues to rotate and releases the stored energy, which, in turn, can accelerate a mass to generate a forward impact. As an example, after sufficient displacement of a mechanical spring or gas spring, in which stored potential energy is increased, the cam and the worm continue to rotate until the worm moves past a second worm end where the worm ceases to act on the mass, releasing the stored energy. Upon release, the stored potential energy accelerates a mass in the forward direction until it comes into operative contact with the point of impact, such as the anvil or another impact surface. Conversely, in embodiments including a bidirectional impacting system, the cam can alternatively rotate in an opposite, second direction, compressing a spring, again storing potential energy within the spring storage system. The cam and the worm, in this example, further continues to rotate to a first worm end where it ceases to act on the spring storage system and the spring storage system can release the stored energy, which, in turn, can accelerate a mass to generate a rearward impact. As an example, after sufficient displacement of the spring, in which stored potential energy of the spring is increased, the cam and the worm continue to rotate until the worm moves past a first worm end where the worm ceases to act on the mass, releasing the stored-energy drive system (or mechanism). Upon release, the potential energy in the stored-energy drive system accelerates a mass in the opposite, rearward direction until it comes into operative contact with the point of impact, such as the anvil or another impact surface.

In an exemplary embodiment, the launched mass (which can incorporate part or all of the stored-energy drive system) separates from a pusher plate or pushing surface prior to its point of impact. Accordingly, in this embodiment, since the entire stored-energy drive system is the launched mass, very high efficiencies were unexpectedly achieved. In a further embodiment which uses a mechanical spring, the compression ratio of the spring is less than about 50% of its free length, and more preferably, less than 40% of its free length. The inventor has found that such compression ratios increase the consistency of the impact energy delivered and reduce the likelihood of permanent spring deformation.

In a further exemplary embodiment, the handle may be repositionable or foldable back to the tool to present an inline tool where the surgeon pushes or pulls on the tool co-linearly with the direction of the broach. This has the advantage of limiting the amount of torque the surgeon may put on the tool while it is in operation. In a further refinement of the hand grip, there may be an additional hand grip for guiding the surgical instrument and providing increased stability during the impacting operation. In a still further embodiment, the tool may be attached to a robot thus eliminating the need for a handle and the tool may use a tethered or remote power source.

In a further exemplary embodiment, a surgical implement (e.g., the adapter, broach, chisel or other end effector) can be rotated to a number of positions while still maintaining axial alignment, as illustrated, for example, in FIG. 9, where the adapter is rotatable in four different positions, each position rotated by 90°. This facilitates the use of the adapter or broach, for example, in various anatomical presentations during surgery.

In an exemplary embodiment, an anvil of the tool includes at least one of two points of impact, a forward striking surface or first surface and a rearward striking surface or second surface, and a guide assembly, such as guide rollers, bearings, or Polytetrafluoroethylene (PTFE) or Teflon tracks to constrain the striker to move in a substantially axial direction. The point of impact of the striker and the resulting force on the surgical tool can be both in the forward and reverse directions. In the bidirectional impacting operation, when a forward force on the surgical tool is generated, the striker moves along the guide assembly and continues in the forward direction. A reversing mechanism can be used to change the point of impact of the striker and the resulting force on the surgical tool. Use of such a reversing mechanism results in a rearward force being exerted on the anvil and/or the broach or other surgical attachment. As used in this context, "forward direction" connotes movement of the striker toward a surgical implement or patient, and "rearward direction" connotes movement of the striker away from the surgical implement or patient. The selectivity of either bidirectional or unidirectional impacting provides flexibility to a surgeon in either cutting or compressing material within the implant cavity in that the choice of material removal or material compaction is often a critical decision in a surgical procedure, as discussed, for example, in U.S. Pat. No. 8,602,124. Furthermore, it was discovered in the use of the inventor's own, previous work that the tool could be used in a broader range of surgical procedures if the reverse impact force could be approximately equal to the forward impact force. In an embodiment, the forward and rearward forces impact at least two separate and distinct points.

In an exemplary embodiment, the anvil and the adapter include a single element, or one may be integral to the other.

In typical impactors, as shown in U.S. Pat. No. 6,938,705, as used in demolition work, varying the speed varies the impact force, making it impossible to maintain constant impact energy, defined as +/31 20%, in variable speed operation. Accordingly, in an exemplary embodiment, the tool includes a control element or controller, which includes an energy adjustment element or mechanism, and which energy adjustment element may control the impact force of the tool by controlling storage and release of energy output from the stored-energy drive mechanism. The energy may be regulated electronically or mechanically (see switch 34 in FIG. 9, for example). Furthermore, the energy adjustment element may be analog or have fixed settings. This control element allows for the precise control of the impacting operation. The energy adjustment element allows a surgeon to increase or decrease the impact energy of the tool according to a patient's profile.

In a further exemplary embodiment, the tool is also capable of controlling the frequency of the striker's impacting movement, using, for example, a mechanical switch 36 illustrated in FIG. 9. By regulating the frequency of the striker, the tool may, for example, impart a greater total time-weighted percussive impact, while maintaining the same impact magnitude. This allows the surgeon better control over the cutting speed of the surgical implement. For example, the surgeon may choose cutting at a faster rate (higher frequency impacting) during the bulk of the surgical implement movement and then slow the cutting rate as the surgical implement approaches a desired depth. In fact, during testing of the tool, it was discovered that a higher frequency impacting rate, such as 3 impacts per second, preferably up to 10 impacts per second, coupled with a constant energy per impact, such as between 2 to 6 joules per second, preferably up to 40 joules per second, allowed the surgeon to better position certain surgical implements. This was seen, for example, in the seating of an acetabular cup, where an impact frequency of at least 3 impacts per second, at an energy of between 2 and 6 joules per second, resulted in far better control of the position of the acetabular cup over the prior art manual hammering technique.

In an example embodiment, the stored-energy drive mechanism, or energy storage and release mechanism, defines points of operation, either mechanically or electrically. As a result, the energy per impact is delivered in accordance with the selected points of operation. In fact, the energy per impact may be controlled to better than 20%. In a further embodiment, timing elements may be incorporated into the system such that the impact is delivered at predetermined frequencies, selectable by the user. Using the electronic control element or controller and precisely controlling the rate of impact allows the surgeon to control the total energy delivered by the tool.

In certain embodiments, the direction of impacting is controlled by a biasing force placed by a user on the tool and detected by a sensor, such as a positioner sensor, on the anvil. For example, biasing the tool in the forward direction results in the launched mass being launched forward and gives forward impacting, whereas biasing the tool in the rearward direction results in the launched mass being launched rearward and gives rearward impacting.

In some embodiments, the tool may have a lighting element to illuminate a work area and accurately position the surgical implement on a desired location on the prosthesis or the implant.

In some embodiments, a bumper is predisposed between a head of the piston and an end of the striker, reducing the impact stress and prolonging the life of the entire assembly.

In some embodiments, the tool also includes a feedback system that warns the user when a bending or off-line orientation beyond a certain magnitude is detected at a broach, chisel, or other end effector or implant interface or the orthopedic implement is not advancing.

In some embodiments, the tool further allows for a replaceable cartridge to vary the impact forces. These cartridges could be rated by the total energy delivered by the stored energy system when actuated by the motor assembly or linear motion converter. As an example, a low power cartridge with a limit in the range of 2 to 3 joules or less could be used for soft or osteoporotic bone. In the case of young, hard bone, a power cartridge with impact energy of 4 or more joules could be selected. By allowing for a variety of cartridges, which in an embodiment could be visually coded according to power, the surgeon would have flexibility in determining the impact energy per cycle by simply selecting the appropriate power cartridge provided with the tool in a kit.

In some embodiments, the tool includes an energy storage and release mechanism that releases energy stored therein at a rate of between 1 to 10 times per second to drive an operably linked surgical implement, a controller configured to monitor and manage storage and release of the energy storage and release mechanism, an adapter to secure the surgical implement, and a thrown mass for delivering an impact force responsive to the released energy to the surgical implement.

In some embodiments, the energy storage and release mechanism includes a barrel or cylindrical cam that rotates to compress and release a spring to generate the impact force. The barrel or cylindrical cam may include a worm protruding from the barrel cam and a cam follower connecting the worm and the spring, where the rotation of the barrel or cylindrical cam pushes the cam follower against the spring and releases the cam follower from the spring. The worm may include a helicoid surface extending between a first worm end and a second worm end. The cam follower may slide on the helicoid surface from the engagement point to the first worm end as the barrel or cylindrical cam rotates.

In some embodiments, the tool includes an energy storage and release mechanism that releases energy stored therein at a rate of between 1 to 10 times per second to drive an operably linked surgical implement, a controller configured to monitor and manage storage and release of the energy storage and release mechanism, an adapter to secure the surgical implement, and a thrown mass for delivering an impact force responsive to the released energy to the surgical implement.

In some embodiments, the energy storage and release mechanism includes a barrel or cylindrical cam that rotates to compress and release a spring to displace the thrown mass and generate the impact force. The barrel or cylindrical cam may include a worm protruding from the barrel or cylindrical cam and a cam follower connecting the worm and the spring, where the rotation of the barrel or cylindrical cam pushes the cam follower against the spring and releases the cam follower from the spring. The worm may include a helicoid surface extending between a first worm end and a second worm end. The cam follower may slide on the helicoid surface from the first worm end to the second worm end as the barrel or cylindrical cam rotates.

These together with other aspects of the present disclosure, along with the various features of novelty that characterize the present disclosure, are pointed out with particularity in the claims annexed hereto and form a part of the present disclosure. For a better understanding of the present disclosure, its operating advantages, and the specific non-limiting objects attained by its uses, reference should be made to the accompanying drawings and detailed description in which there are illustrated and described exemplary embodiments of the present disclosure.

The forgoing general description of the illustrative implementations and the following detailed description thereof are merely exemplary aspects of the teachings of this disclosure, and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings.

DETAILED DESCRIPTION OF ILLUSTRATIVE EMBODIMENTS

Figure 1:
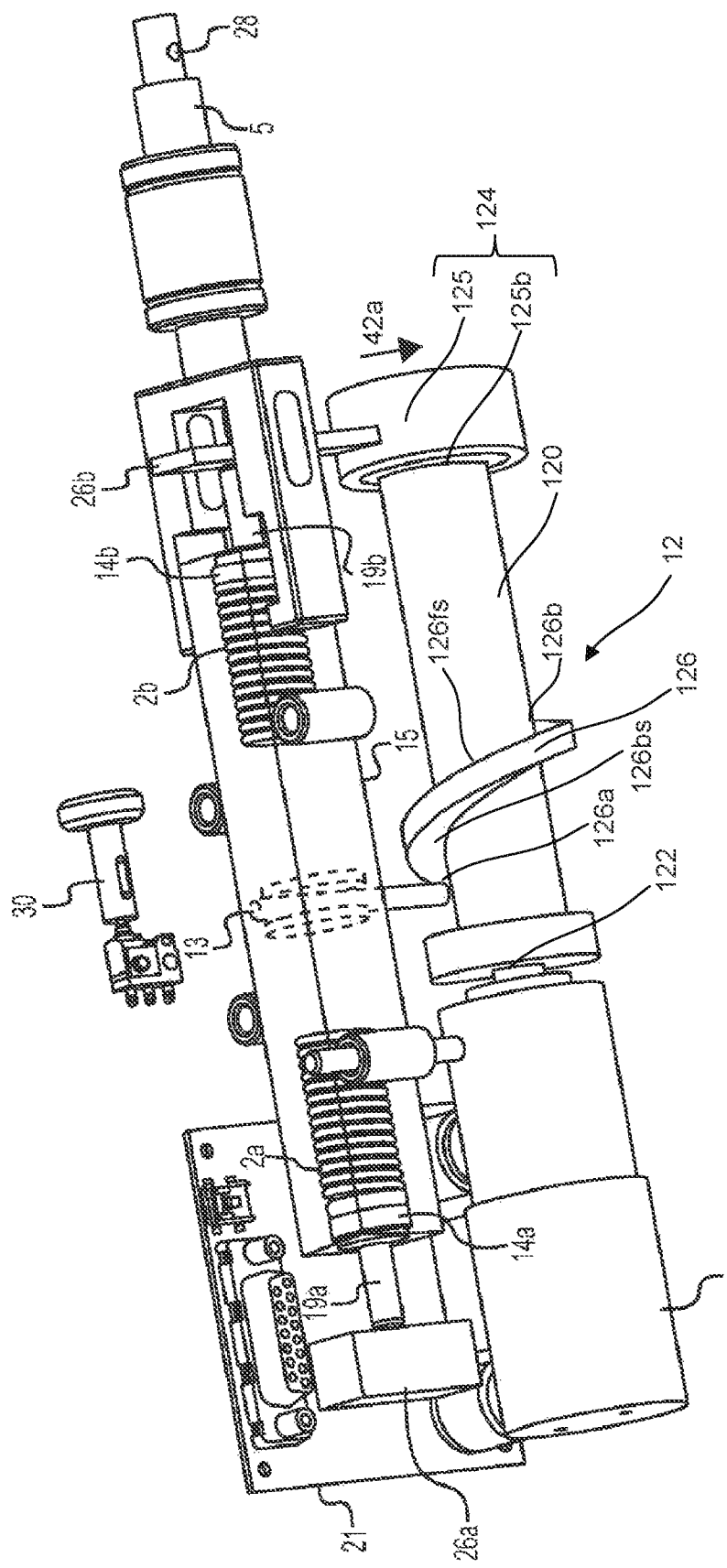
FIG. 1 illustrates a perspective view of an orthopedic impacting tool in accordance with an exemplary embodiment of the present disclosure in which a mechanical spring assembly system is used for generating a forward impact force.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventor intends that that feature or function may be deployed, utilized or implemented in connection with the alternative embodiment unless the feature or function is incompatible with the alternative embodiment.

A motor-driven orthopedic impacting tool is provided with controlled percussive impacts. The motor may be electric, such as a brushless, autoclavable motor such as those generally available from Maxon Motor® and/or Portescap®. The motor may be battery-operated. The energy supply to the orthopedic impacting tool may provide wireless portability for the orthopedic impacting tool. The tool may include the capabilities to perform single and multiple impacts, as well as impacting of variable and varying directions, forces, and frequencies. In some embodiments, the impact energy is adjustable. In certain embodiments, the impact is transferred to a surgical implement such as a broach, chisel, or other end effector connected to the tool.

In some embodiments, the tool includes a housing. The housing may securely cover and hold at least one component of the tool and may be formed of a material suitable for surgical applications, such as aluminum or Polyphenylsulfone (PPSF or PPSU), also known as Radel®. In some embodiments, the housing contains a motor assembly, at least one reducing gear, a spring element, a striker or launched mass, a control circuit or module, an anvil, a first or forward striking surface for forward impact, and a different, second or rearward striking surface for rearward impact. The motor assembly may include a linear motion converter to convert a rotary motor drive. The spring element may be a mechanical or gas spring.

The tool further may include a handle portion with an optional hand grip for comfortable and secure holding of the tool, or a suitable mount interface for integrating the tool into a robotic assembly while in use, and an adapter, a battery, a positional sensor, a directional sensor, and a torsional sensor. The tool may further deliver focused illumination by way of a semiconductor light source, such as an LED, or traditional incandescent light source to provide light in the surgical work area in which a surgeon employs the tool. The anvil may be coupled to a surgical implement broach, chisel or other end effector known in the art through the use of an interfacing adapter, which adapter may have a quick connect mechanism to facilitate rapid change of different broaching sizes. The anvil may further include a locking rotational feature to allow the tool to be positioned in different fashions as to gain tissue clearance to tool features such as the handle.

In some embodiments, an axis of the launched or thrown mass is aligned axially, along the direction of movement, to within 20 degrees of the axis of the adapter, and more preferably, to within 10 degrees of the axis of the adapter. Such axial alignment is significant in terms of maximizing the energy transferred to the surgical implement, as well as minimizing the generation of off-axis forces, which can contribute to adverse surgical outcomes, such as fractures.

Referring now generally to FIGS. 1 through 7, in some embodiments, a bidirectional impact force may be generated using a mechanical spring assembly system, as illustrated, for example, in FIG. 1. In other embodiments, a single mechanical spring assembly may be used. FIG. 1 shows a perspective view of an orthopedic impacting tool in accordance with an embodiment of the present disclosure in which a motor 8 of the mechanical spring assembly system, in combination with a linear motion converter, which includes a barrel or cylindrical cam 12 and a cam follower 13, actuates a first spring piston 19a (hereinafter referred to as the "first piston 19a") and/or a launched mass or striker 15, in order to ultimately generate a forward impact force. It is to be noted that the piston generally refers to a thrusting or push off element and can have any of a number of shapes.

The barrel cam 12 can include a cylindrical portion 120 mounted longitudinally on a shaft 122 extending between the motor 8 and a bearing support 124, and a worm 126 protruding radially from the cylindrical portion 120 and helicoidally along a length of the cylindrical portion 120 from a first worm end 126a to a second worm end 126b.

The bearing support 124 can include a housing 125 supported by the second pusher plate 26b and a bearing nested in the housing 125 to support the shaft 122.

The worm 126 can include a backward surface 126bs, e.g. surface facing a first pusher plate 26a, and a forward surface 126fs of the worm 126, e.g. surface facing the second pusher plate 26b, that contacts the cam follower 13 and forces the cam follower 13 to follow a rectilinear movement between the first worm end 126a and the second worm end 126b as the worm 126 rotates.

Figure 2:
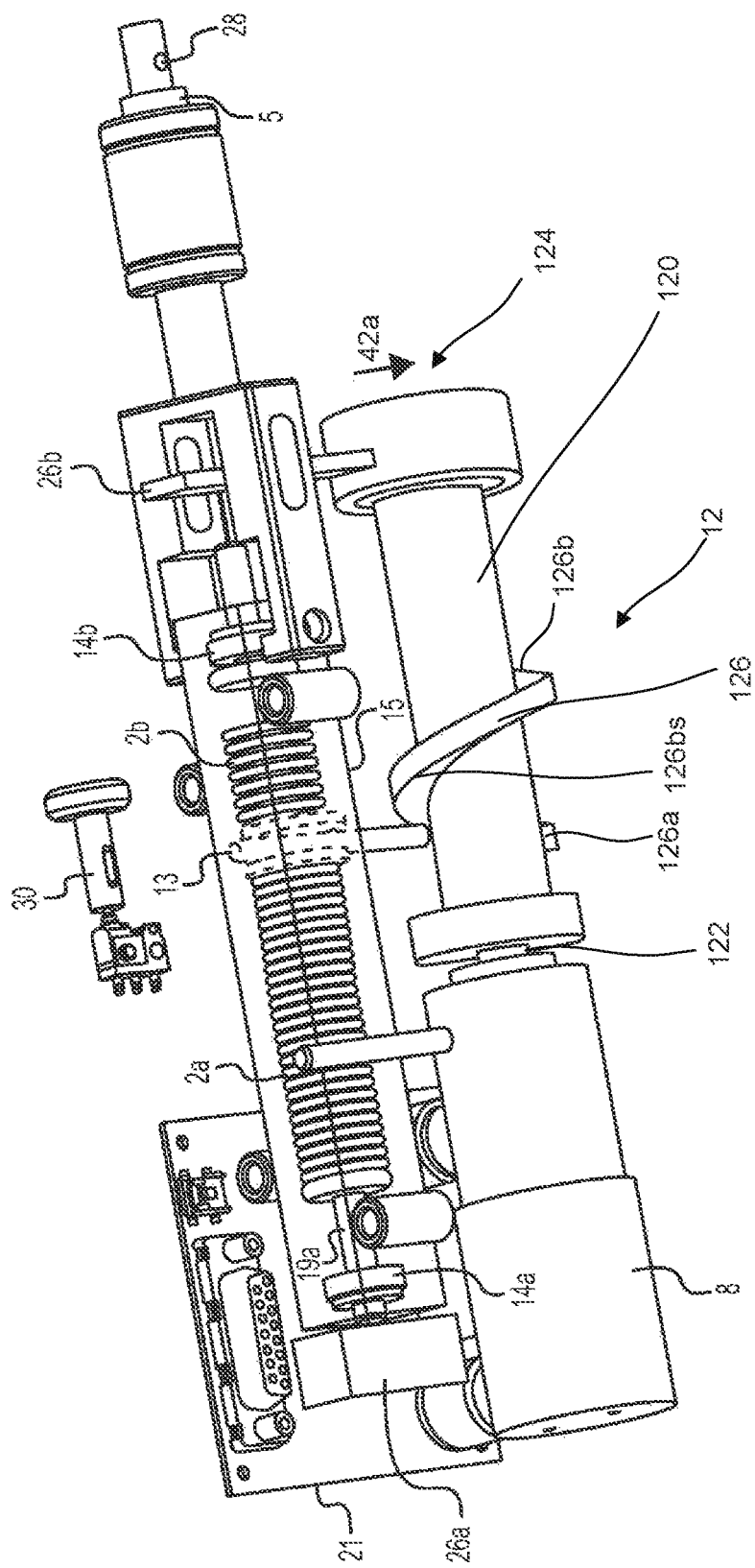
FIG. 2 shows an exemplary embodiment of the tool in FIG. 1 in which the barrel or cylindrical cam positions the piston in the operative position for release for a forward impact.
Figure 3:
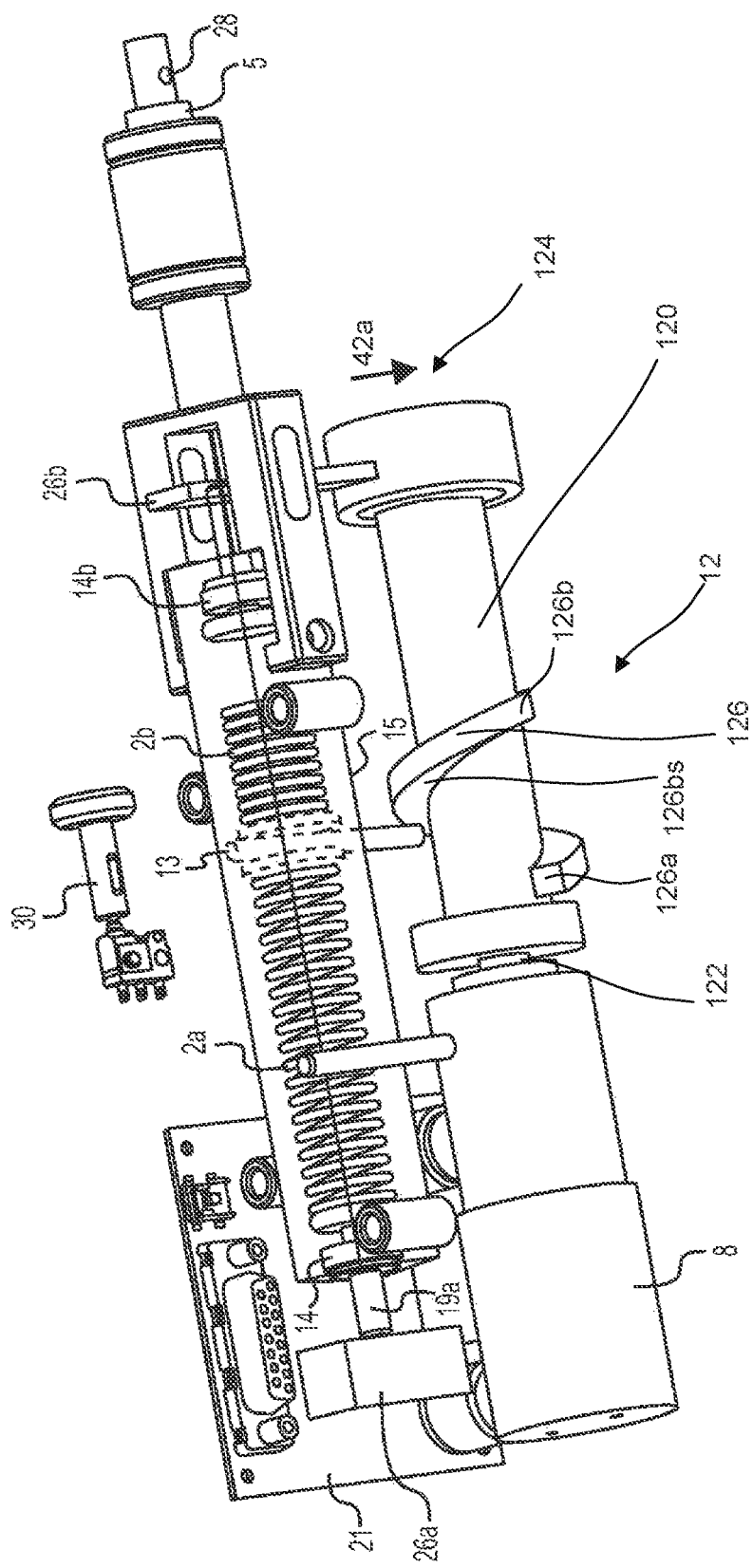
FIG. 3 shows an exemplary embodiment of the tool in FIG. 1 in which after the stored-energy has been released, a launched mass is accelerated towards a point of impact in a forward direction.

The cam follower 13 can be displaced along the worm 126 in the backward direction, e.g. towards the first pusher plate 26a, by having the cam follower 13 contacting a backward surface 126bs of the worm 126, e.g. surface facing the pusher plate 26a, and having the worm 126 rotating in a first direction 42a, as illustrated in FIGS. 1-3. Similarly, the cam follower 13 can be displaced along the worm 126 in the forward direction, e.g. towards the second pusher plate 26b, by having the cam follower 13 contacting the forward surface 126fs of the worm 126 and having the worm 126 rotating in a second direction 42b, as illustrated in FIGS. 4-7.

The barrel cam 12 can enhance efficiency of the orthopedic impacting tool by allowing the motor 8 to rotate with larger angles compared to a conventional linear motion converter that may rely on conventional vertical cams that hit the cam follower 13 through small repetitive strokes. That is, the barrel cam 12 allows the use of more radians of rotation for the motor to get the energy and thus, reduces the current drain on the battery significantly. Accordingly, a single primary battery could be used in certain embodiments by utilizing the advantages provided by the barrel cam 12 in the reduction of the current drain.

In addition, the barrel cam 12 can prevent the use of gear assemblies, e.g. straight bevel gear assembly, as the barrel cam 12 can be directly mounted onto the shaft 122 and thus enhance efficiency of the orthopedic tool.

The spring assembly system further includes, in some embodiments, an anvil 5. The first piston 19a engages a first spring 2a, which can for example be either a mechanical or gas spring. In the mechanical spring assembly system, the deflection in relation to a free length of the spring is preferably less than 50%. Music wire or, more preferably, stainless steel or titanium are suitable materials for the spring. Preferably, the spring is a compression spring, although other types of springs are contemplated. In the gas spring assembly system, the gas spring operates under pressure in a range of about 100 to 3000 psi, for example. The gas spring is preferably initially charged with a non-oxidizing gas, such as nitrogen, or an inert gas, such as argon. Advantageously, nitrogen has a lower permeation rate through seals of the gas spring, resulting in a potentially longer shelf life for the seals and the spring itself.

FIG. 2 further illustrates the example tool of FIG. 1 in which the barrel cam 12 used for actuating the first piston 19a has the first piston 19a "cocked" in the operative position ready for release, or stated another way, the motor 8 rotates the shaft 122 which rotates the barrel cam 12, the first worm end 126a of the worm 126 contacts the cam follower 13 and the cam follower 13 linearly slides along the backward surface 126bs and compresses the first piston 19a against the first pusher plate 26a, thus storing potential energy within the first spring 2a. In the "cocking phase" the first piston 19a, in combination with the launched mass or striker 15, contacts and is pushed by the cam follower 13, which is driven by the worm 126 of the barrel cam 12 that rotates under the action of the motor 8. As the barrel cam 12 and worm 126 continue to rotate, energy stored inside the first spring 2a increases until the first worm end 126a moves past the cam follower 13 to let the cam follower 13 jump from the first worm end 126a to the second worm end 126b. The striker (or launched mass) 15 is now free to travel under the stored potential energy of the first spring 2a. In particular, after a sufficient displacement of the first piston 19a, and after the barrel cam 12 releases the first piston 19a and/or the launched mass 15, the first piston 19a moves in the forward direction, and, at the same time, accelerates the launched mass or striker 15, which is in contact with the face of the first piston 19a. As shown, for example, in FIG. 3, the first piston 19a releases from the striker 15, launching it towards the anvil 5. It was unexpectedly discovered by the inventor that the release of the striker 15 from the pusher plate 26a, which essentially creates a portion of free flight during its travel, dramatically reduces the recoil generated and experienced by the surgeons' hands, resulting in a more controllable tool. The striker 15, which has been launched towards the end of the tool that is proximate to the end surgical implement or patient, then percussively impacts a first surface or forward striking surface of the anvil 5. A maximum displacement of the anvil when in contact with the striker may be less than 15 mm. It was unexpectedly discovered during testing of the tool that surgeons achieved better results, in terms of more precise and accurate movements, when a maximum forward displacement of the anvil was limited to less than 15 mm, and more preferably, less than 10 mm. By limiting the stroke, the resulting surgical procedure was more accurately executed and in better alignment with the surgical target, as compared to larger strokes. In stark contrast, use of a mallet during surgery, for example, often leads to displacements of 20 mm or more, resulting in less accuracy during the procedure.

The impact of the striker 15 on the anvil 5 communicates a forward impact force to an adapter (not shown) and thereby to the broach, chisel, or other orthopedic instrument. The launched mass or striker 15 may be constructed from a suitable material such as steel or any other material having similar properties, lending it to repeated impacting.

In some embodiments, a ratio of a weight or mass of the launched mass or striker 15 to a weight or mass of the tool is preferably less than 25%, and the launched mass 15 has an amount of free flight before contact, both factors contributing to a further reduction in the recoil generated. It was unexpectedly discovered by increasing the weight or mass of the launched mass in relation to the weight or mass of the anvil that the impact energy was more effectively transferred to the surgical implement. For example, when a ratio of the mass of the launched mass to the mass of the anvil is less than 25%, the resultant transfer efficiency is extremely low, i.e., less than 50% for a typical coefficient of restitution of 0.8. As such, it was found that mass ratios under 50% resulted in the lowest transfer efficiencies of the impact.

In certain embodiments, as illustrated in FIG. 2, for example, as the striker 15 moves in the rearward direction, towards the pusher plate 26a, a bumper 14a functions as a stopper to prevent an end face of the piston 19a from impacting the striker 15. The bumper 14a absorbs the impact of the piston 19a immediately before the launched mass or striker 15 is launched in the forward direction. It was discovered by the inventor in the course of the development that without having the piston 19a come to rest on the bumper 14a, excessive wear occurred resulting in failure of the piston 19a. Accordingly, such bumper 14a prevents damage to the spring assembly system, particularly the piston 19a, during repeated operation. The bumper 14a can be one of a plastic or more preferably a rubber or urethane material.

As discussed above, it has been determined by the inventor that his previous designs occasionally resulted in the surgical implement seizing in a biological cavity and the impact of the striker 15 in the rearward direction may be insufficient to dislodge the tool. Further, it was discovered that the rearward force needs to be communicated as a sharp retracting impact in order to dislodge the surgical implement. Accordingly, in certain embodiments having a bidirectional impacting system, there are at least two different impacting surfaces, and, when the tool is being pulled away from the cavity, the striker 15 will impact an alternate surface on the anvil 5 and thereby communicate a rearward force on the anvil 5.

Figure 4:
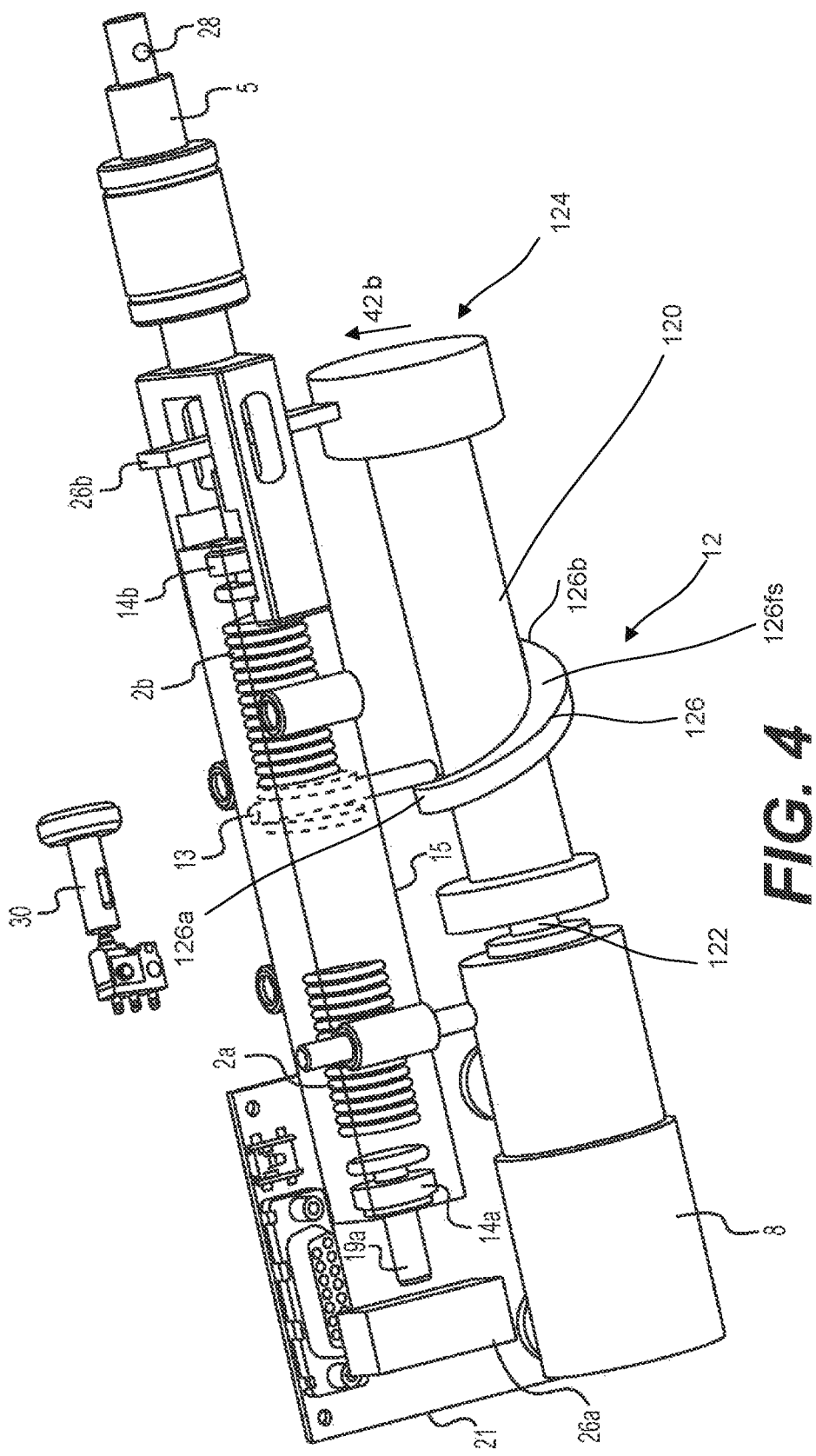
FIG. 4 illustrates a perspective view of an orthopedic impacting tool in accordance with an exemplary embodiment of the present disclosure in which a mechanical spring is used for generating a rearward impact force.
Figure 5:
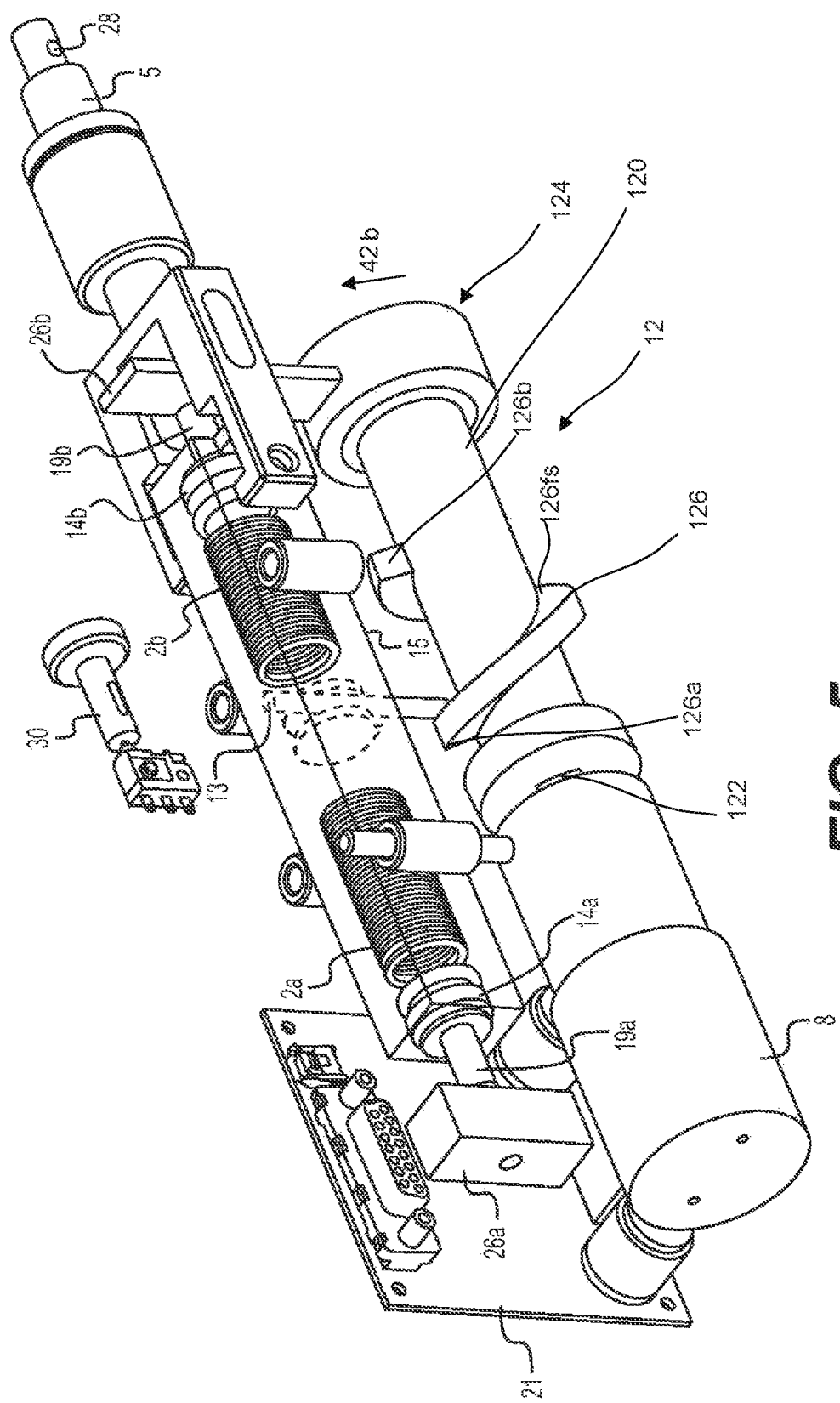
FIG. 5 shows another perspective view of the impacting tool in FIG. 4 from an alternate angle.
Figure 6:
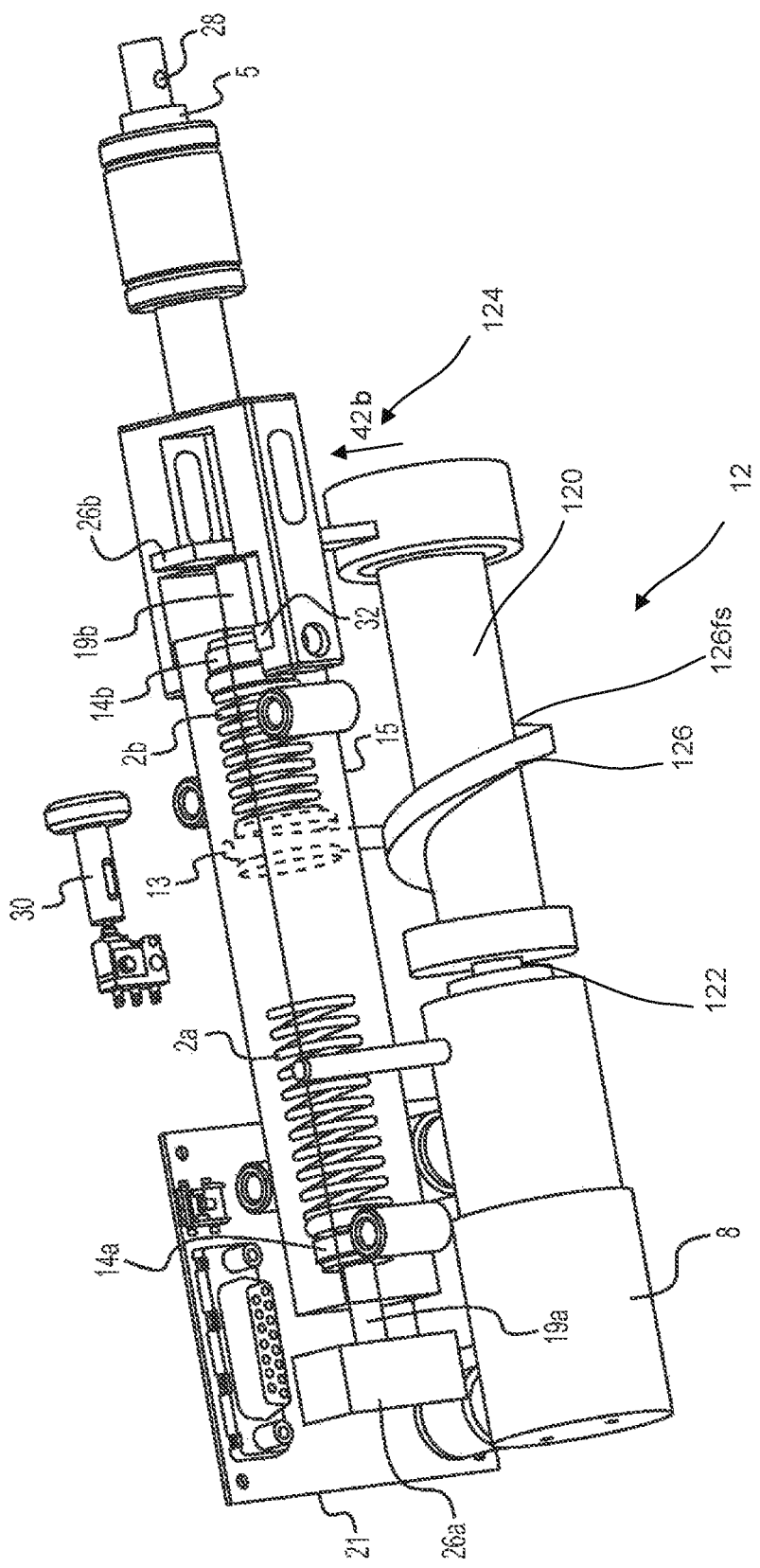
FIG. 6 shows an exemplary embodiment of the tool in FIG. 4 in which the barrel or cylindrical cam of the mechanical spring positions piston in the operative position for release for a rearward impact.
Figure 7:
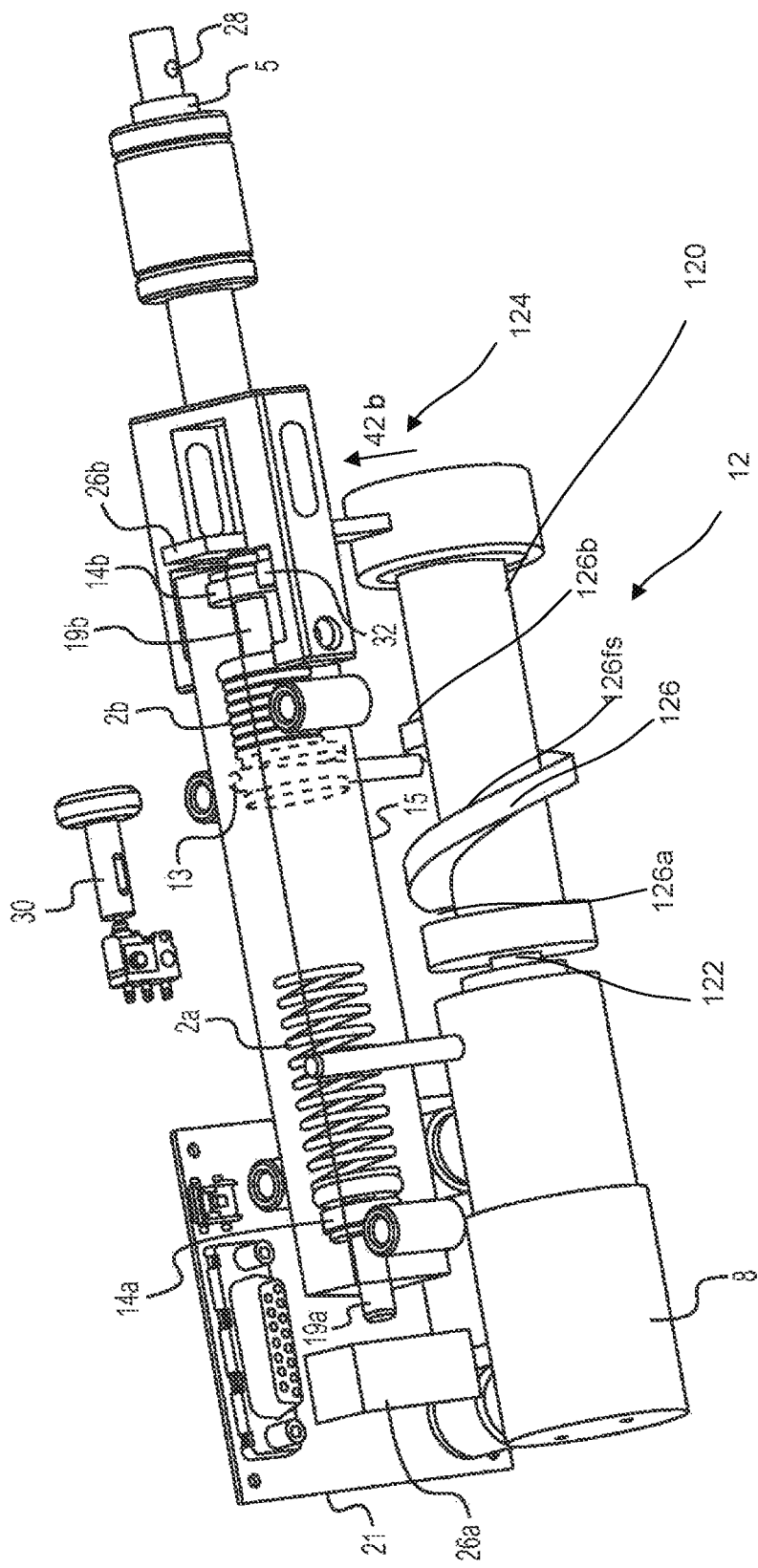
FIG. 7 shows an exemplary embodiment of the tool in FIG. 4 in which after the spring has been released, a launched mass is accelerated towards a point of impact in a rearward direction.

FIGS. 4-7 illustrate a perspective view of an example orthopedic impacting tool in which the cam follower 13 contacts the forward surface 126fs and the motor 8 of the mechanical spring assembly system rotates the barrel cam 12 to launch the mass or striker 15 and generate a rearward impact force. FIG. 4, and similarly FIG. 5, which is another perspective view of the impacting tool shown in FIG. 4 from an alternate angle, illustrates the barrel cam 12 in midcourse, e.g. when the cam follower 13 is between the second worm end 126b and the first worm end 126a. As the motor 8 continues to rotate the barrel cam 12 and the worm 126, the cam follower 13 continues to move towards the second worm end 126b, a second spring piston 19b (hereinafter referred to as the "second piston 19b") engages a second spring 2b and is compressed against a second pusher plate 26b, thus storing potential energy within the second spring 2b. The second piston 19b, in turn, is "cocked" in the operative position ready for release (see FIG. 6). In the "cocking phase" the second piston 19b, in combination with the launched mass or striker 15, contacts and is pushed by the cam follower 13. As shown in FIGS. 6 and 7, for example, an end surface of the striker or launched mass 15 includes a pair of extensions or protrusions 32 integral with the launched mass 15 or provided as separate elements connected (e.g., bolted) to the launch mass 15. As the barrel cam 12 and the worm 126 continue to rotate energy stored inside the second spring 2b increases until the second worm end 126b of worm 126 moves past the cam follower 13 to let the cam follower 13 jump from the second worm end 126b to the first worm end 126a (see FIG. 7, for example). The striker or launched mass 15 is now free to travel under the stored potential energy of the second spring 2b. In particular, after a sufficient displacement of the second piston 19b, and after the barrel cam 12 releases the second piston 19b and/or the launched mass 15 combination, the second piston 19b moves in a rearward direction, i.e., a direction toward the point of impact, and, at the same time, accelerates the launched mass or striker 15, which is in contact with the face of the second piston 19b. As shown, for example, in FIG. 7, the second spring 2b releases from the striker 15, launching it away from the end of the tool that is proximate to the surgical implement or patient, with the extensions or protrusions 32 of the launched mass 15 impacting an alternate, second or rearward striking surface of the anvil 5, thereby percussively imparting a rearward impact force on the anvil 5.

Similar to the spring bumper 14a illustrated in FIG. 2 and discussed above, a spring bumper 14b shown in FIG. 4 also functions as a stopper to prevent an end face of the piston 19b from impacting the striker 15, as the piston 19b moves in the forward direction. The bumper 14b absorbs the impact of the piston 19b immediately before the launched mass or striker 15 is launched in the rearward direction. As discussed above, it was discovered by the inventor in the course of the development that without having the piston 19b come to rest on the bumper 14b, excessive wear occurred resulting in failure of the piston 19b. Accordingly, such bumper 14b prevents damage to the spring assembly system, particularly the piston 19b, during repeated operation. Similar to bumper 14a, the bumper 14b can be one of a plastic or more preferably a rubber or urethane material.

Figure 10:
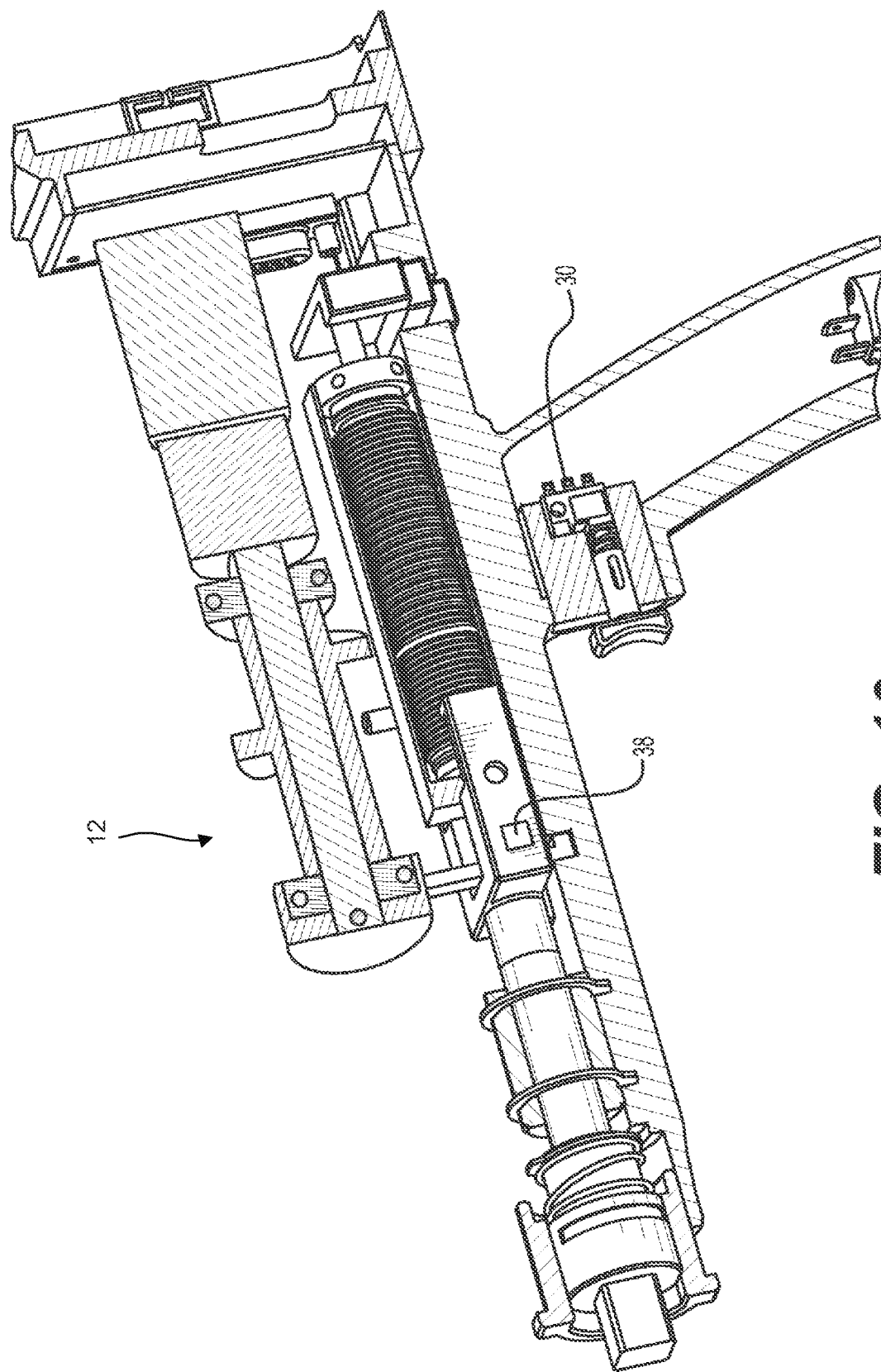
FIG. 10 shows an exemplary embodiment of the tool with a positional sensor used in determining the direction of impact.

In some embodiments, a direction of the force on the anvil 5 is controlled by the user's (such as a surgeon's) manual force on the tool detected by a sensor 28. The sensor, for example, can be a positional sensor 38 on the anvil 5, as shown in FIG. 10. For example, biasing the tool in the forward direction results in the launched mass or striker 15 being launched forward and gives forward impacting, whereas biasing the tool in the rearward direction results in the striker 15 being launched rearward and gives rearward impacting.

In some embodiments, as the barrel cam 12 assembly completes its course, e.g. the cam follower 13 is displaced along the backward surface 126fs from the first worm end 126a to the second worm end 126b or along the forward surface 126bs from the second worm end 126b to the first worm end 126a, it preferably activates the sensor 28, as shown, for example, in FIG. 5, coupled operatively to a controller 21. The sensor 28 assists in the regulation of the preferred cyclic operation of the barrel cam 12. For example, the sensor 28 may signal the motor 8 to stop such that the barrel cam 12 is at or near a point of minimal potential energy storage. Thus, in one complete cycle, a forward or a rearward impacting force may be applied on the broach, chisel, or other end effector, or on the implant or prosthesis. In a further embodiment, it may be advantageous to insert a delay or count the number of impacts for any give procedure before starting the next cycle, making it possible to accurately control the speed of impacting, and, in turn, allowing the surgeon to accurately control the rate of energy delivery in any given operation. In a still further embodiment, it may be advantageous to stop the barrel cam 12 near a point of maximum potential energy storage to reduce a latency in the surgeons' hands. Latency, as defined, is the time between when the surgeon (or user) activates the orthopedic impacting tool and the tool actually delivers an impact. It has been determined by the inventor that latencies of around 100 milliseconds or less appear essentially as an instantaneous response. By stopping the barrel cam 12 at a point where at least part of the potential energy has been stored, the tool has the effect of near instantaneous release of the potential energy upon actuation of a tool trigger 30.

In a further embodiment, an additional sensor (not shown) may be used to detect that the surgical implement is not progressing during the percussive impacting. If the surgical implement has stopped advancing for a period of less than 10 seconds, or more preferably, less than 3 seconds, the tool can provide feedback to the surgeon. Such feedback may be provided in the form of lights, reduction or stoppage of the impacting, or other means. A surgeon will then have the opportunity to evaluate the procedure and determine whether to re-initiate the impacting operation.

Figure 8:
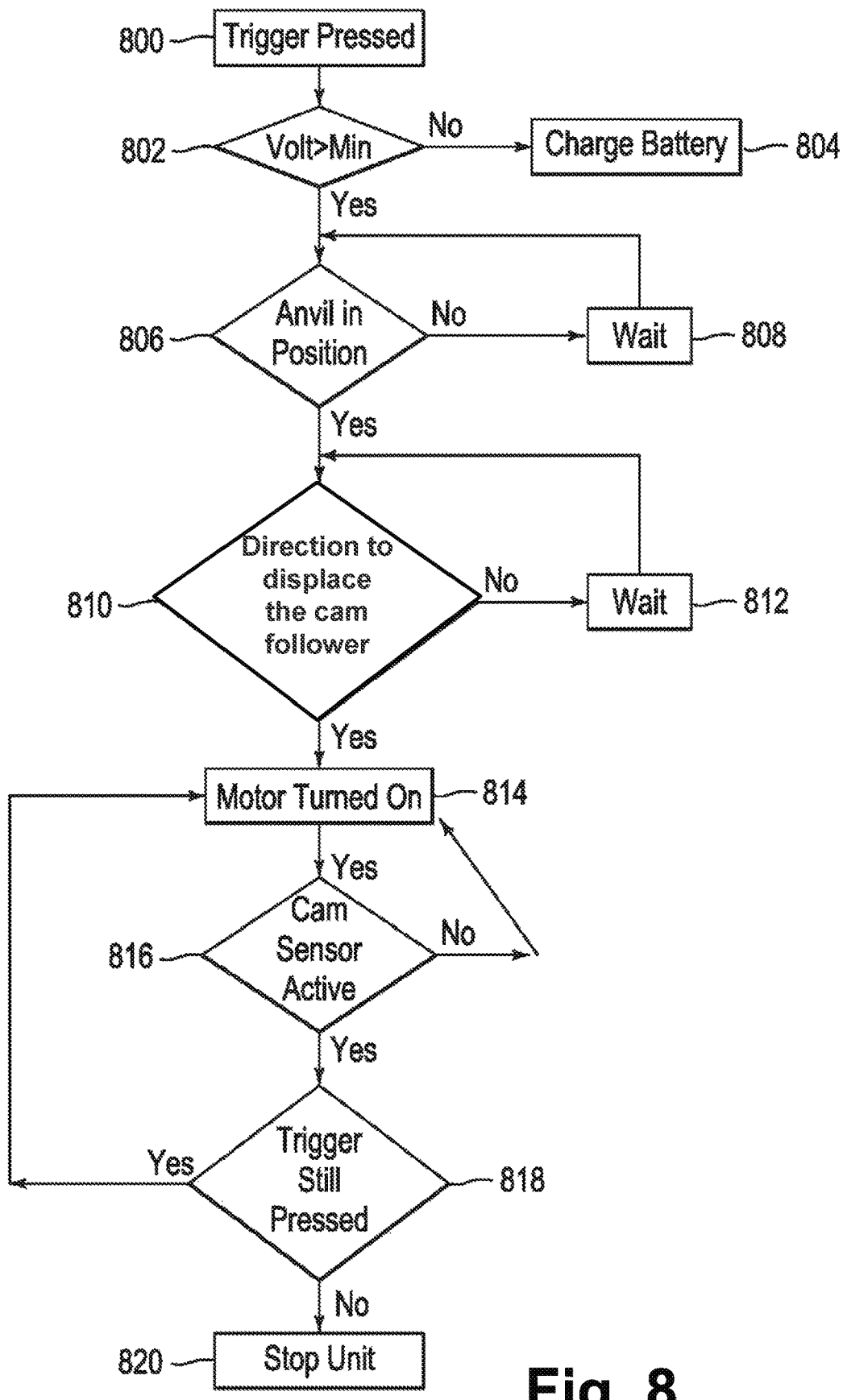
FIG. 8 is an exemplary flow chart illustrating a cyclic operation of the orthopedic impacting tool in accordance with an exemplary embodiment of the present disclosure.
Figure 9:
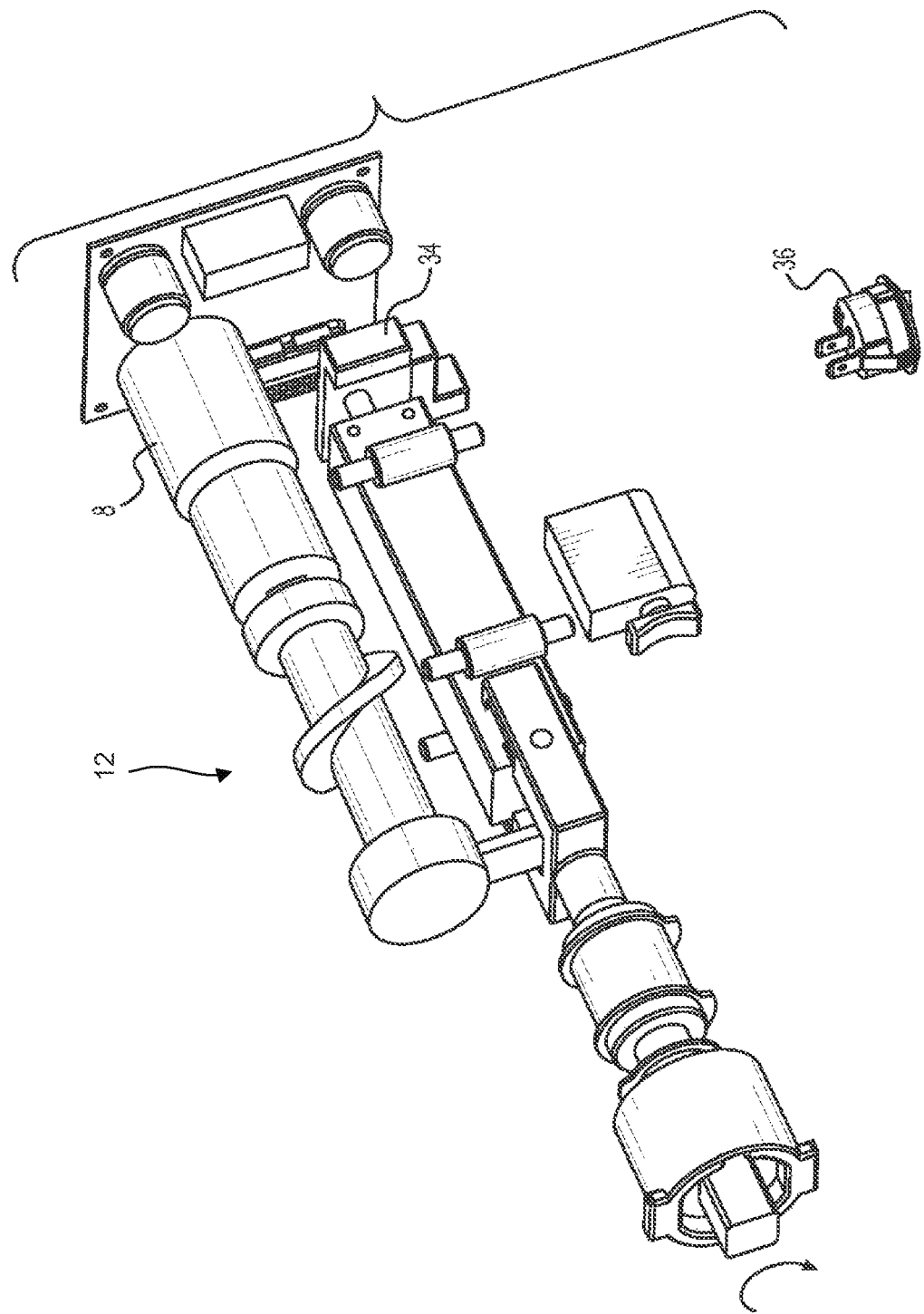
FIG. 9 shows an exemplary embodiment of the tool with mechanical switches used for controlling energy and frequency-related parameters.

FIG. 8 is a flow chart illustrating an example cyclic operation of an orthopedic impacting tool. The controller 21, in some embodiments, operates with firmware implementing the cyclic operation described in FIG. 8, which results in the orthopedic impacting tool being able to generate a repeatable, controllable impacting force. The controller 21 can include, for example, intelligent hardware devices, e.g., processing circuitry such as a data processor, microcontroller or FPGA device, for example those made by Intel® Corporation (Santa Clara, Calif.) or AMD® (Sunnyvale, Calif.). Other type of controllers can also be utilized, as recognized by those skilled in the art.

In some embodiments, at the start of a cycle, a trigger is pressed in step 800 to initiate operation. For example, a surgeon or a robotic controller may actuate the trigger. In some embodiments, the trigger is a manual trigger, such as a compressible button or lever. In other embodiments, the trigger is an electrical trigger, such as a signal issued by a robotic controller to initiate operation. The trigger, for example, may be activated upon a sensor detecting ready placement of a surgeon's hand on a handle or grip of the orthopedic tool.

In some embodiments, it is determined in step 802 whether the orthopedic impacting tool is charged and ready for use. If a voltage of a local power source, such as a battery, is determined to be charged at less than a threshold minimum, for example, then the local power source may be set to charge in step 804. In some examples, a charge indicator lamp may be lit or flashed, and/or a tone audibly generated to indicate that the orthopedic tool requires charging.

In some embodiments, if the voltage of the local power source is greater than the threshold minimum, then it is next determined in step 806 whether an anvil and/or broach or other surgical attachment is correctly positioned relative to a cavity of the patient's bone. For example, a sensor may determine whether the anvil and/or surgical attachment are proximate to the cavity. In another example, a patient profile may determine an orientation, for example of a robotic controller, for positioning the anvil and/or other surgical attachment relative to the cavity of the patient's bone.

In some embodiments, if the anvil and/or surgical attachment is correctly positioned, the operation moves on to step 810; otherwise, the system waits until the position is corrected in step 808.

Next, in step 810, in some embodiments it is determined whether a decision has been made as to which direction to displace the cam follower based on whether the tool is being used to generate a forward impact force or a rearward impact force. Determination, in one example, may be based at least in part upon a biasing force placed by a user on the tool. The biasing force, for example, may be detected by a sensor, such as a positioner sensor, on the anvil and/or connector for the surgical implement. In another example, a signal may be issued by an automated system selecting an initial direction. Further, in some implementations, rather than determining a direction, the direction may be automatically initiated based upon last direction of impact (e.g., the opposite direction of the most recent force applied, in a circumstance where stored force exists).

If the direction to displace the cam follower has been decided, in some embodiments, then the motor assembly activates in step 814 in order to complete an impact cycle; otherwise, the system waits until the displacement has been determined in step 812.

Once the motor assembly completes an impact cycle, in some embodiments, step 816 determines whether a cam sensor has been activated. If the sensor has been activated, then the process proceeds to step 818 to determine whether the trigger is still maintained; otherwise, the process returns to step 814 to allow the motor to continue rotating until the cam sensor has been activated. If a trigger is maintained in step 818, then the operation cycles back to step 814 where the motor continues drive, causing the tool to continue generating impacts; otherwise, the operation of the orthopedic impacting tool ceases at step 820.

Advantageously, the piston and spring assembly system does not need or use a detent or a magnet for generating a higher energy impact. The magnitude of the energy output from the system is consistent for any given set of operating conditions, taking into consideration factors such as the spring constant, the spring preload force, and/or the total compression of the spring during the operational cycle. The impact energy output from the stored-energy drive system, in some implementations, is between 1 to 10 joules, which varies no more than 20%, and preferably, no more than 10%, for a given operational cycle. For example, the impacting tool may include a spring with a spring constant of 100 pounds per inch, operating at a preload force of 100 pounds, and with a cam stroke of 0.5 inches, resulting in the stored-energy drive system outputting a total impact energy of about 7.1 joules, minus frictional and other losses.

In embodiments having a bidirectional impacting system, the piston and spring assembly mechanism may be approximately 80% efficient in the rearward direction compared to prior designs, which were about 20% efficient. For example, in the inventor's previous designs, a forward impact of approximately 3.5 J of energy would result in a rearward impact of only 0.4 J of energy, resulting in a loss of nearly 80% of the energy, which was not ideal.

It has been determined by the inventor that the mass ratios and materials used for the launched or thrown mass, the anvil, and the adapter are significant in terms of the how effectively the kinetic energy of the thrown mass is conveyed to the surgical implement. For purposes of certain embodiments, the ratio of the delivered energy to the surgical implement as a function of the kinetic energy in the thrown mass or striker is referred to as the transfer function. The transfer function is used as a measure of performance, in terms of how efficiently the tool is performing broaching, impacting, or extraction surgical procedures. For example, in one design in which the thrown mass, anvil, and adapter were all made of hardened stainless steel, the ratio of the energy conveyed to the surgical implement to the kinetic energy of the thrown mass, or the transfer function, was found to be less than 50%. By increasing the mass ratio of the thrown mass to the impacted mass (the sum of the mass of the anvil, the adapter, and the surgical implement), the efficiency of the system, in particular, the transfer function, was increased to greater than 60%, and in many cases, close to 75%.

Further, it was unexpectedly discovered that by keeping the compression ratio of the spring to less than 50% of its free length, and more preferably less than 30%, that spring life and impact consistency were maximized. One unexpected effect was generating much more consistent impacts between the striker 15 and the anvil 5, which was a result of the spring not permanently deforming. Indeed, the consistency of the impacts, as generated by the gas or mechanical spring, was found to be within +/−10% of the nominal design value since the impact energy was only slightly influenced by the environmental conditions.

The tool, in some embodiments, facilitates controlled continuous impacting, which impacting is dependent on a position of the trigger switch 30 operatively coupled to the power source or motor, for example. For such continuous impacting, after the trigger switch is activated, and depending on the position of the trigger switch 30, the tool may go through complete cycles at a rate proportional to the position of the trigger switch, for example. Thus, in either the single impact or continuous impacting operational modes, the creation or shaping of the surgical area may be easily controlled by the surgeon.

As discussed previously, in certain embodiments the tool is capable of varying the amount of impact energy per cycle by way of, for example, choosing an appropriate internal pressure for a replaceable gas spring cartridge (not shown) or a different mechanical spring for the stored-energy drive system. It will be appreciated that since the drive mechanism for imparting potential energy into the spring is a fixed stroke, different impact energies can be obtained in any given surgery by simply using a spring cartridge with a different preload or spring constant. In further embodiments, an element, such as a linear cam, can be used to vary the amount of compression in the stored-energy drive system by changing a location of the pusher plate, for example. By controlling the impact energy, the surgeon has greater flexibility during a procedure.

In some embodiments, the tool is designed to facilitate extraction of well-fixed implants or "potted" broaches. In such embodiments, the barrel cam 12 is rotated in the second, clockwise direction 42b and launches the mass or striker 15 such that the movement of the striker 15 is away from the patient, causing a retraction or rearward force on the anvil 5.

The tool, in further embodiments, includes a compliance element (not shown) inserted between the striker 15 and the anvil 5. Preferably, the compliance element is a resilient material that recovers well from impact and imparts minimal damping on the total energy. As an example, a urethane component could be inserted at the interface where the striker 15 impacts the anvil 5. In another example, the compliance element may be inserted in such a fashion that it only reduces the impact force in the forward direction and does not affect the desire for a sharp impact force in the rearward direction. This type of compliance element can limit the peak force during impact to preclude such peaks from causing fractures in the patient's bone, yet maintain the high peak force necessary to be able to retract stuck broaches or other surgical implements.

In some embodiments, the impactor is coupled to a robot, for example, thus potentially eliminating the need for a portable power source (battery) and or hand grip on the tool.

In some embodiments, the coupling of the adapter (not shown) to the tool includes a linkage arrangement or other adjustment mechanisms known in the art such that the position of the surgical implement (broach, chisel or other end effector) can be modified without requiring the surgeon to rotate the tool.

The orthopedic tool disclosed herein provides various advantages over the prior art. It facilitates controlled impacting at a surgical site, which minimizes unnecessary damage to a patient's body and allows precise shaping of an implant or prosthesis seat. The tool also allows the surgeon to modulate the direction, force, and frequency of the impacts, which improves the surgeon's ability to manipulate and control the tool. For example, the orthopedic tool can be used solely for retraction purposes depending on the surgical procedure being performed. Similarly, the tool can be customized to have different forward and reverse impact forces. In a mechanical spring assembly system, for example, different gauge springs can be used for forward and reverse impact. The force and compliance control adjustments of the impact settings allow a surgeon to set the force of impact according to a particular bone type or other profile parameter of a patient. Further, the improved efficiency and reduced linear motion converter loads allow use of smaller batteries and lower cost components. The tool thereby enables proper seating or removal of the prosthesis or implant into or out of an implant cavity. Further, the piston and spring assembly provides a simple means for adjusting the impact energy for a particular surgery. Additionally, since the spring assembly is essentially governed by the mechanical properties of the spring, such as the deflection, preload and spring constants, the resulting tool imparts a predictable impact energy independent of the operational speed. Furthermore, in embodiments in which the gas spring cartridge is replaceable, elements subject to high wear, such as seals and pistons, can be replaced in each surgery, resulting in a more robust, long life tool and reducing points of failure.

Figure 11:
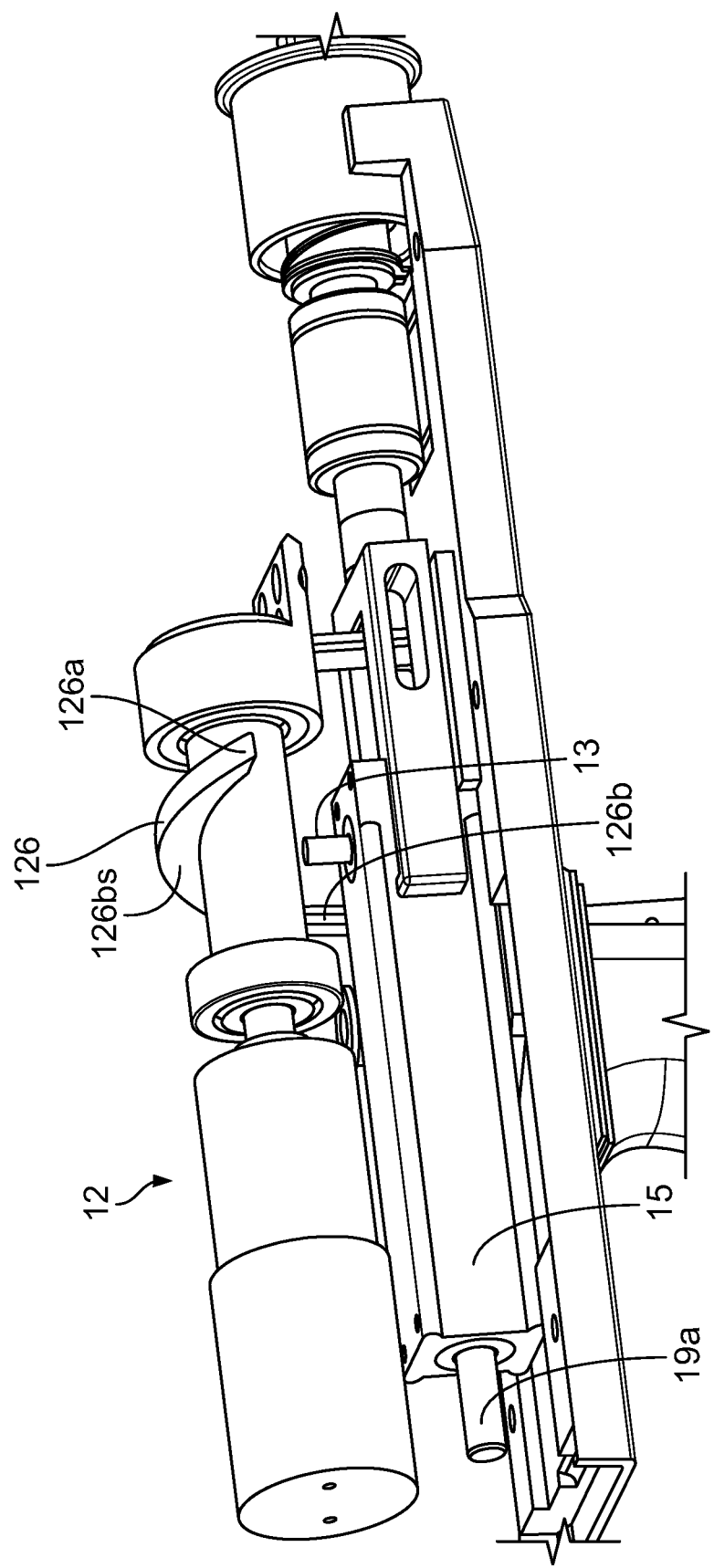
FIG. 11 illustrates a perspective view of the orthopedic impacting tool in accordance with an exemplary embodiment of the present disclosure in which a single spring is used for generating a forward impact force and a rearward impact force.
Figure 12:
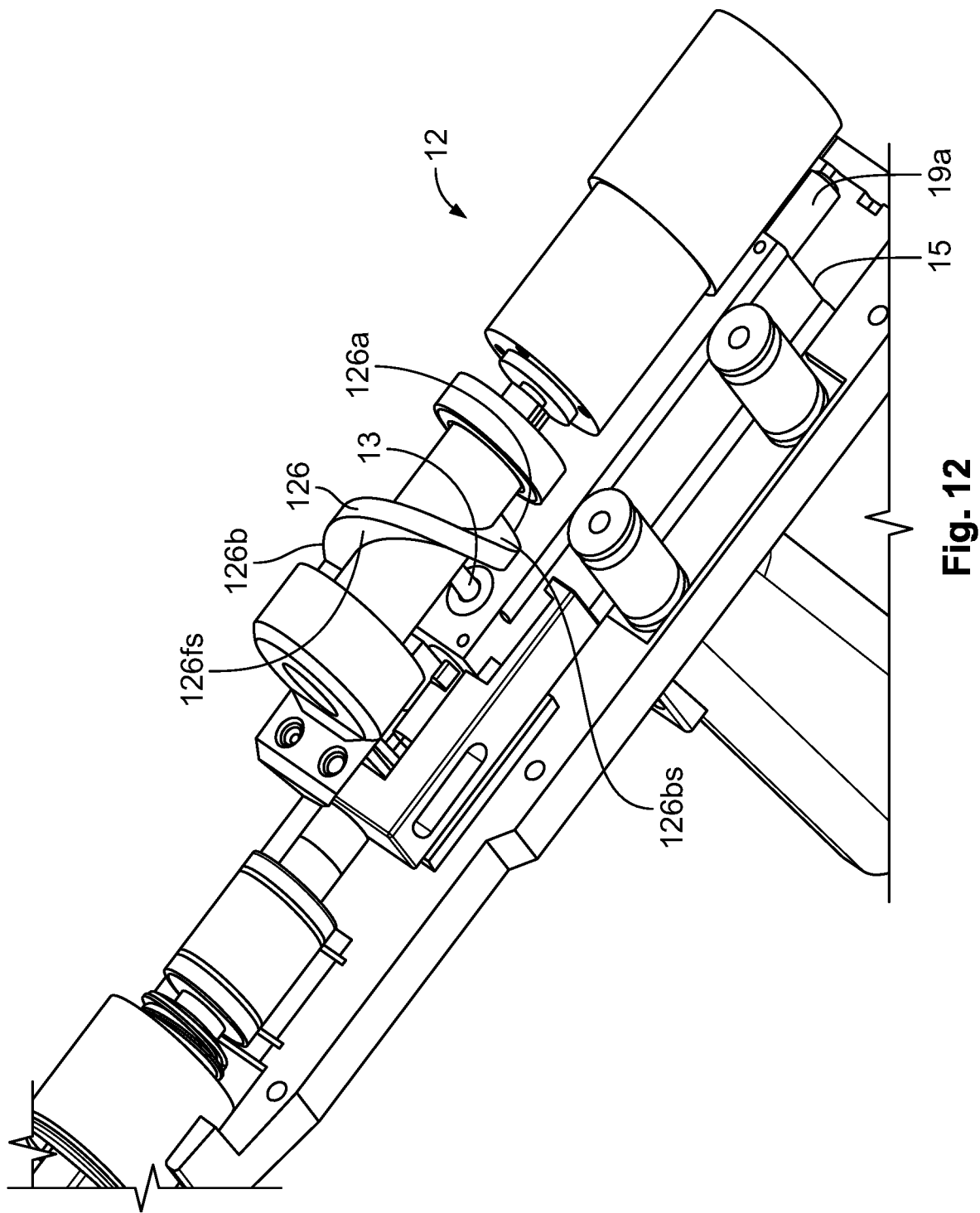
FIG. 12 shows another perspective view of the impacting tool in FIG. 11 from an alternate angle.
Figure 13:
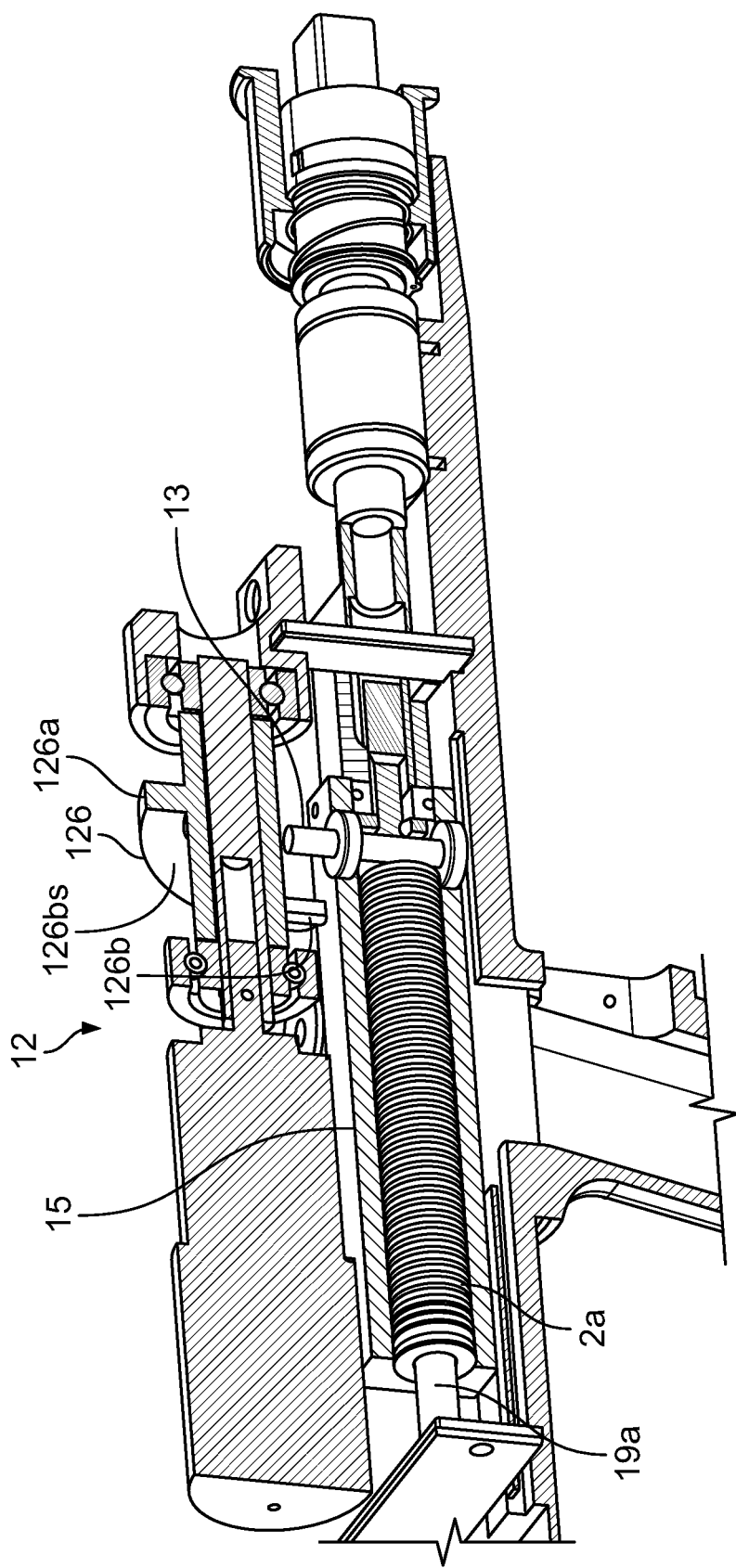
FIG. 13 shows a cross sectional view of the impacting tool in FIG. 11.

FIGS. 11-13 illustrate a perspective view of another example orthopedic impacting tool in which a single spring is employed to generate the forward impact force and the rearward impacting force. In some embodiments, the cam follower 13 is affixed to the spring 2a to compress the spring 2a in the backward direction to generate the forward impact force and to pull the spring 19a in the forward direction to generate the rearward impact force. The worm 126 may wrap around the surface of the cylindrical portion 120 less than 360 degrees, such as an amount approximating 270 degrees. The sections of the cylindrical portion 120 that are not covered by the worm 126, for example a 90 degree section of the cylindrical portion 120, may facilitate travel of the striker or launched mass 15 in the forward and backward directions.

When the cam follower 13 is in contact with the backward surface 126bs of the worm 126, in some embodiments, the cam follower slides along the backward surface 126bs from the first worm end 126a to the second worm end 126b and compresses the spring 2a. As the barrel cam 12 and the worm 126 continue to rotate, energy stored inside the spring 2a increases until the second worm end 126b of worm 126 moves past the cam follower 13 to let the cam follower 13 jump from the second worm end 126b to the first worm end 126a. The striker or launched mass 15 is now free to travel in the forward direction under the stored potential energy of the spring 2a to generate the forward impact force.

When the cam follower 13 is in contact with the forward surface 126fs of the worm 126, in some embodiments, the cam follower slides along the forward surface 126fs from the second worm end 126b to the first worm end 126a and extends the spring 2a. As the barrel cam 12 and the worm 126 continue to rotate, energy stored inside the spring 2a increases until the first worm end 126a of worm 126 moves past the cam follower 13 to let the cam follower 13 jump from the first worm end 126a to the second worm end 126b. The striker or launched mass 15 is now free to travel in the backward direction under the stored potential energy of the spring 2a to generate the rearward impact force.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A surgical impacting tool, comprising:
   a spring element configured to release energy stored therein to drive an operably linked surgical implement;
   a rotary cam mechanism configured to rotate to compress and release the spring element to generate an impact force;
   a helical drive mechanism protruding radially outward from the rotary cam mechanism and configured to rotate with the rotary cam mechanism;
   a cam follower coupled to the spring element and extending radially outward therefrom to contact a surface of the helical drive mechanism;
   an adapter configured to secure the surgical implement to the surgical impacting tool; and
   a means for delivering to the adapter the impact force responsive to the released energy, wherein the spring element includes a first spring and a second spring axial aligned with the first spring, and the cam follower is disposed between the first spring and the second spring.

2. The surgical impacting tool of claim 1, wherein the spring element is configured to release energy stored therein at a rate of between 1 and 10 times per second.

3. The surgical impacting tool of claim 1, wherein the spring element comprises a replaceable spring cartridge.

4. The surgical impacting tool of claim 1, wherein the helical drive mechanism comprises a worm gear.

5. The surgical impacting tool of claim 1, wherein the rotary cam mechanism comprises a barrel cam.

6. The surgical impacting tool of claim 1, further comprising a motor configured to drive the rotation of the rotary cam mechanism, and a controller configured to control the motor and monitor and manage storage of the energy in and release of the energy from the spring element; and
   a mechanical trigger mechanism for activating the controller.

7. The surgical impacting tool of claim 1, wherein the rotation of the rotary cam mechanism is configured to push the cam follower against the spring element and release the cam follower from the spring element.

8. The surgical impacting tool of claim 1, wherein the spring element comprises a mechanical spring having a compression ratio of less than 50% of a free length of the mechanical spring.

9. The surgical impacting tool of claim 1, further comprising a motor configured to drive the rotation of the rotary can mechanism, and a controller configured to control the motor and monitor and manage storage of the energy in and release of the energy from the spring element, wherein after the delivery of the impact force the controller is configured to stop the rotary cam mechanism in a position where at least part of the potential energy has been stored by the spring element, thereby providing a latency upon activation of the surgical impacting tool of up to about 100 milliseconds.

10. The surgical impacting tool of claim 1, wherein the means for delivering the impact force comprises a striker activated by a piston, wherein the piston is configured to be actuated by the rotation of the rotary cam mechanism.

11. The surgical impacting tool of claim 10, wherein the piston, upon actuation, comes to rest on a bumper element.

12. The surgical impacting tool of claim 10, wherein a ratio of a weight of the striker to a combined weight of the adapter and the surgical implement secured therein is less than 25%.

13. The surgical impacting tool of claim 1, wherein the helical drive mechanism extends along the rotary cam mechanism from a first terminal end of the helical drive mechanism to a second terminal end of the helical drive mechanism.

14. The surgical impacting tool of claim 13, wherein the rotation of the helical drive mechanism is configured to cause the cam follower to move from one of the first and second terminal ends to the other of the first and second terminal ends.

15. The surgical impacting tool of claim 14, wherein the cam follower is configured to move past the other of the first and second terminal ends while the helical drive mechanism is rotating; and
   the spring element is configured to release the energy stored therein in response to the cam follower moving past the other of the first and second terminal ends.

16. The surgical impacting tool of claim 15, wherein, in response to the spring element releasing the energy stored therein, the cam follower is configured to jump from the other of the first and second terminal ends to the one of the first and second terminal ends.

17. A surgical impacting tool, comprising:
a spring element configured to release energy stored therein to drive an operably linked surgical implement;
a rotary cam mechanism configured to rotate to compress and release the spring element to generate an impact force;
a helical drive mechanism protruding radially outward from the rotary cam mechanism and configured to rotate with the rotary cam mechanism;
a cam follower coupled to the spring element and extending radially outward therefrom to contact a surface of the helical drive mechanism;
an adapter configured to secure the surgical implement to the surgical impacting tool; and
a means for delivering to the adapter the impact force responsive to the released energy, wherein the means for delivering the impact force comprises a means for delivering both a forward impact force and a reverse impact force, wherein the reverse impact force is equal or greater to the forward impact force.

18. The surgical impacting tool of claim 17, wherein the means for delivering the impact force comprises a striker activated by a piston, wherein the piston is configured to be actuated by the rotation of the rotary cam mechanism.

19. The surgical impacting tool of claim 17, wherein the helical drive mechanism comprises a worm gear.

20. The surgical impacting tool of claim 17, wherein the rotary cam mechanism comprises a barrel cam.

21. The surgical impacting tool of claim 17, further comprising a motor configured to drive the rotation of the rotary cam mechanism, and a controller configured to control the motor and monitor and manage storage of the energy in and release of the energy from the spring element; and
a mechanical trigger mechanism for activating the controller.

22. A surgical impacting tool, comprising:
a spring element configured to release energy stored therein;
a rotary cam mechanism configured to rotate to compress and release the spring element to generate an impact force;
a helical drive mechanism protruding radially outward from the rotary cam mechanism and configured to rotate with the rotary cam mechanism;
a cam follower coupled to the spring element and extending radially outward therefrom to contact a surface of the helical drive mechanism, the rotation of the helical drive mechanism being configured to move the cam follower along the surface from a first position, in which the cam follower contacts one terminal end of the helical drive mechanism, to a second position, in which the cam follower contacts an opposite terminal end of the helical drive mechanism;
an adapter configured to secure the surgical implement to a surgical impacting tool; and
a striker for delivering to the adapter the impact force responsive to the released energy, wherein the spring element includes a first spring and a second spring axially aligned with the first spring, and the cam follower is disposed between the first spring and the second spring.

23. The surgical impacting tool of claim 22, wherein the cam follower is configured to move from the second position to a third position past the opposite terminal end while the helical drive mechanism is rotating; and
the spring element is configured to release the energy stored therein in response to the cam follower moving past the opposite terminal end and thereby cause the cam follower to move from the third position to the first position.

24. The surgical impacting tool of claim 22, wherein the helical drive mechanism comprises a worm gear, the rotary cam mechanism comprises a barrel cam, and the spring element comprises one of a gas spring and a mechanical spring.

* * * * *